United States Patent [19]
Weng et al.

[11] Patent Number: 5,404,293
[45] Date of Patent: Apr. 4, 1995

[54] CONE BEAM RECONSTRUCTION USING HELICAL DATA COLLECTION PATHS

[75] Inventors: Yi Weng; Gengsheng L. Zeng; Grant T. Gullberg, all of Salt Lake City, Utah

[73] Assignee: The University of Utah, Salt Lake City, Utah

[21] Appl. No.: 956,805

[22] Filed: Oct. 5, 1992

Related U.S. Application Data

[63] Continuation-in-part of Ser. No. 713,719, Jun. 11, 1991, Pat. No. 5,170,439.

[51] Int. Cl.$^6$ .................. G06F 15/42; A61B 8/00; A61B 6/02
[52] U.S. Cl. .................. 364/413.19; 382/6; 364/413.16
[58] Field of Search ............ 364/413.19, 413.13, 364/413.15, 413.2, 413.16; 128/660.01, 660.06

[56] References Cited

U.S. PATENT DOCUMENTS

| | | | |
|---|---|---|---|
| 4,205,375 | 5/1980 | Inouye et al. | 364/413.2 |
| 4,606,004 | 8/1986 | Crawford et al. | 382/6 |
| 4,616,318 | 10/1986 | Crawford | 364/413.2 |
| 4,894,775 | 1/1990 | Kritchman et al. | 364/413.16 |
| 4,979,111 | 12/1990 | Nishimura | 364/413.16 |
| 5,170,439 | 12/1992 | Zeng et al. | 364/413.16 |

*Primary Examiner*—Gail O. Hayes
*Attorney, Agent, or Firm*—Fay, Sharpe, Beall, Fagan, Minnich & McKee

[57] ABSTRACT

Radiation passing through a cone beam collimator is received by a radiation detector (10) such as a gamma camera head, as the gamma camera head is moved in a helical orbit. Data g(n,u,v) collected during the helical orbit is scaled (42) to scaled data G(n,u,v). A first partial derivative $\partial G(n,u,v)/\partial u$ is taken (46u) with respect to a horizontal direction and a second partial derivative $\partial G(n,u,v)/\partial v$ is taken (46v) with respect to a vertical direction. The partial derivatives are linearly combined (48) by being multiplied by sine and cosine values of an angle $\alpha$ between the horizontal direction u and an arbitrary direction p in the detector plane to form partial derivatives $\partial G(n,u,v)/\partial p$. The coordinate system of the derivatives is converted (60) from the (n,u,v) coordinate system to an (n,$\alpha$,p) coordinate system. The first derivatives are projected (62) i.e. summed row by row, onto a q axis which is perpendicular to the p arbitrary direction. The one-dimensional projection arrays are rebinned (70) to form first derivative Radon domain data $R'(\vec{\theta},\rho)$. A second derivative $R''(\vec{\theta},\rho)$ is taken (74) of the Radon domain data. The second derivative Radon domain data is backprojected (80) into an image memory (82) and displayed on a video monitor (84).

17 Claims, 4 Drawing Sheets

CONE BEAM RECONSTRUCTION USING HELICAL DATA COLLECTION PATHS

The present invention is a continuation-in-part of U.S. application Ser. No. 07/713,719, filed Jun. 11, 1991, now U.S. Pat. No. 5,170,439.

BACKGROUND OF THE INVENTION

The present invention relates to the art of diagnostic imaging. It finds particular application in conjunction with single photon emission computed tomography (SPECT) scanners with cone-beam collimation for medical diagnostic imaging and will be described with particular reference thereto. It is to be appreciated, however, that the invention will have other applications in which cone-beam type data is reconstructed into an image representation for medical, quality assurance, and other examinations. Although described in conjunction with emission radiation sources which emit radiation from the subject, it will be appreciated that the present invention is also applicable to reconstructing image representation from transmission radiation sources which transmit radiation through a subject.

Cone-beam collimators are commonly used with single photon emission computed tomography and other gamma camera devices. The cone-beam collimator diverges outward from a subject toward the scintillation crystal or detector head. This enables a large fraction of the detector head crystal face to be utilized when imaging relatively small regions of the patient, e.g. the heart. This effective magnification produces a combination of resolution and sensitivity gains over images formed using parallel or fan beam collimators.

Most commonly, cone-beam projection data is converted into image representations using a technique developed by Feldkamp, Davis, and Kress which is described in "Practical Cone-Beam Algorithm", J. Opt. Soc. Am. Vol. I, pp. 612–619 (1984). The Feldkamp technique uses an algorithm which was derived using approximations of a fan beam formula. A fan beam commonly lies in a single plane, but diverge in that plane. When multiple fan beams are used concurrently, the planes are substantially parallel. In this manner, the radiation paths diverge along one axis and are parallel in the other axis of the plane of reception.

Feldkamp, et al. use a convolution and backprojection method which assumes that the focal point orbit is a circle. However, if the focal point of the collimator follows a single, planar orbit, the obtained data is not sufficient for an exact three-dimensional reconstruction. The insufficiency in the amount of collected data causes distortions and artifacts in the resultant image. There are three kinds of artifacts in the images reconstructed by the Feldkamp, et al. algorithm: a) reduced activity on non-central slices; b) cross-talk between non-central adjacent slices; and, c) undershoots in the transverse direction.

In order to generate a complete or sufficient set of data, every plane which passes through the imaging field of view must also cut through the orbit of the focal point at least once. See Tuy "An Inversion Formula for Cone-Beam Reconstruction", SIAM J. Appl. Math. Vol. 43, pp. 546–552 (1983). The single planar orbit of Feldkamp does not satisfy this condition.

Once the projection data complete, one reconstruction approach is to convert the cone-beam projections to Radon transforms and use the Radon inversion formula to reconstruct the image. This technique involves rebinning or sorting of the cone-beam data into another format. See Grangeat "Analysis d'un Systeme D'Imagerie 3D par Reconstruction a Partir De X en Geometrie Conique" Ph.D. Thesis l'Ecole Nationale Superieure Des Telecommunications (1987).

Others have proposed mathematical improvements to the reconstruction algorithms. For example, the cone-beam data sets can be inverted if one assumes that for any line that contains a vertex point and a reconstruction point, there is an integer M (which remains constant for the line) such that almost every plane that contains this line intersects the geometry exactly M times. See Smith "Cone-Beam Tomography: Recent Advances and a Tutorial Review", Optical Engineering, Vol. 29 (5), pp 524–534 (1990). However, this integer requirement condition is too restrictive for practical application.

The present invention provides an exact reconstruction algorithm for reconstructing data from a helical orbit, which satisfies the sufficiency condition and overcomes the above-referenced problems.

SUMMARY OF THE INVENTION

In accordance with the present invention, a new and improved cone beam reconstruction technique is provided. To collect one set of data, a focal point of a cone beam detection system is moved along a helical orbit. The data provided along the helical orbit provides a complete set of data. More specifically, a partial derivative of the data is taken with respect to each arbitrary axis in the plane of the detector head. The partial derivative is projected onto an orthogonal axis in the detector plane. The derivative of the projection data is rebinned into a first derivative in the Radon domain. The second derivative of the Radon domain data is taken and the second derivative Radon domain data is backprojected into three-dimensional image space.

In accordance with a more limited aspect of the present invention, the data is scaled and weighted prior to generating the partial derivatives.

In accordance with another more limited aspect of the present invention, partial derivatives of the data are taken with respect to the horizonal and vertical axes. The partial derivatives with respect to the vertical and horizontal axes are linearly combined in accordance with a sine/cosine relationship with the arbitrary axis. The linearly combined derivatives define the partial derivative along the arbitrary vector direction.

In accordance with another more limited aspect of the present invention, the partial derivative along the arbitrary vector direction is projected along an axis perpendicular to the arbitrary vector direction within said plane.

One advantage of the present invention is that the resultant images are reconstruction algorithm artifact free.

Another advantage of the present invention is that the reconstruction is exact.

Another advantage of the present invention is that the raw data can be generated using conventional hardware which moves detector heads in a circular orbit and linearly along the patient.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
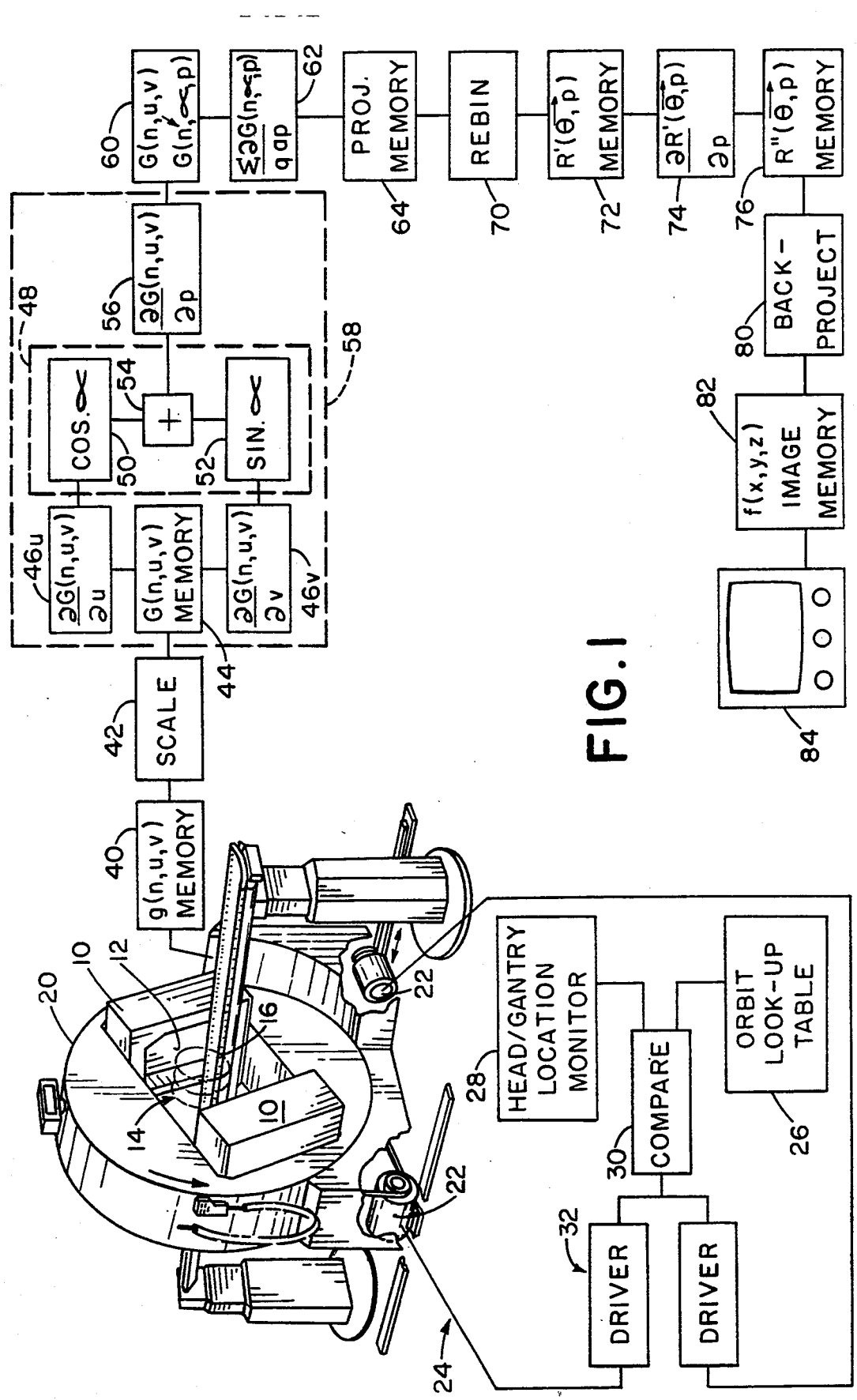
FIG. 1 is a diagrammatic illustration of a SPECT camera system in accordance with the present invention.

With reference to FIG. 1, a cone-beam radiation detection means, such as one or more gamma camera heads 10, each with a cone-beam collimator 12, is mounted to move rotationally around and linearly along an examination region 14. The cone-beam collimator 12 has a plurality of paths defined by bores in a solid lead sheet or by lead vanes which focus at a focal point 16. The cone-beam collimator is oriented such that the focal point 16 is disposed across the examination region 14 from a subject therein. Radiation emanating from the subject or passing through the subject follows diverging paths through the collimator 12 to the gamma camera head 10 or other detector. In this manner, a relatively small region of the subject is projected onto a relatively large region of a crystal face of the detector head 10, i.e. an effective magnification.

The detector heads 10 are mounted on a gantry means or portion 20. The gantry means includes a plurality of motor drives 22 which can be operated individually or in combination in order to move the detector heads along selectable orbits. The heads are rotated along a circular orbit and the gantry is translated to move the heads axially along the subject. An orbit controller 24 generates motor control signals for each of the motors to cause the heads to move along the selected orbit. More specific to the illustrated embodiment, the orbit controller includes a look-up table 26 which is preprogrammed with the appropriate positions which the detector heads and gantry should take to move the focal point 16 along the spiral orbit. A current position sensing means 28 monitors the current position of the detector head(s), such as by monitoring the angular position around the subject, the radial position toward and away from the subject, and the longitudinal position along the subject. A comparing means 30 compares the look-up table values with the actual rotational and longitudinal positions of the detector heads and gantry. A series of motor drivers 32 supply motive power to the motors or linear drive means 22 until the monitored current position matches the desired position from the look-up table. Optionally, descriptions of a plurality of orbits are selectively loadable into the look-up table 24.

The gantry or an associated control console includes a data processing means for processing the output data from the detector head(s). More specifically, each detector head conventionally includes a scintillation crystal that is viewed by an array of photomultiplier tubes. Each time a radiation event occurs, the radiation passing through the collimator and striking the crystal causes a light flash or scintillation. The photomultiplier tubes nearest the scintillation respond with proportional output signals. Position and energy resolving circuitry connected to the photomultiplier tubes determine the energy and position, hence the ray or direction along which the radiation travelled from the radiation event within the subject through the collimator to the detector head. Due to the cone-beam collimator, there is a direct relationship between the position on the scintillation crystal at which the radiation was received and the directional vector $\vec{a}$ of the ray. See FIG. 2.

Output data g(n,u,v) from the detector head during the helical orbit F is stored in a projection data memory 40. In the projection data coordinate system, n is the index of the views, i.e. an angular orientation around the helix; v is an axis along the patient, i.e. parallel to the patient support couch; and u is coordinate of the detector head 10 perpendicular to the axis v. In the preferred embodiment, the axes u and v are horizontal and vertical axes, respectively. A scaling means 42 scales or weights the projection data to generate weighted projection data G(n,u,v) which is stored in a weighted projection data memory means 44. Preferably, this scaling or weighting means multiplies the projection data g(n,u,v) by a constant based on the geometry of the gantry and the system as described in Equation (9) below.

Figure 3:
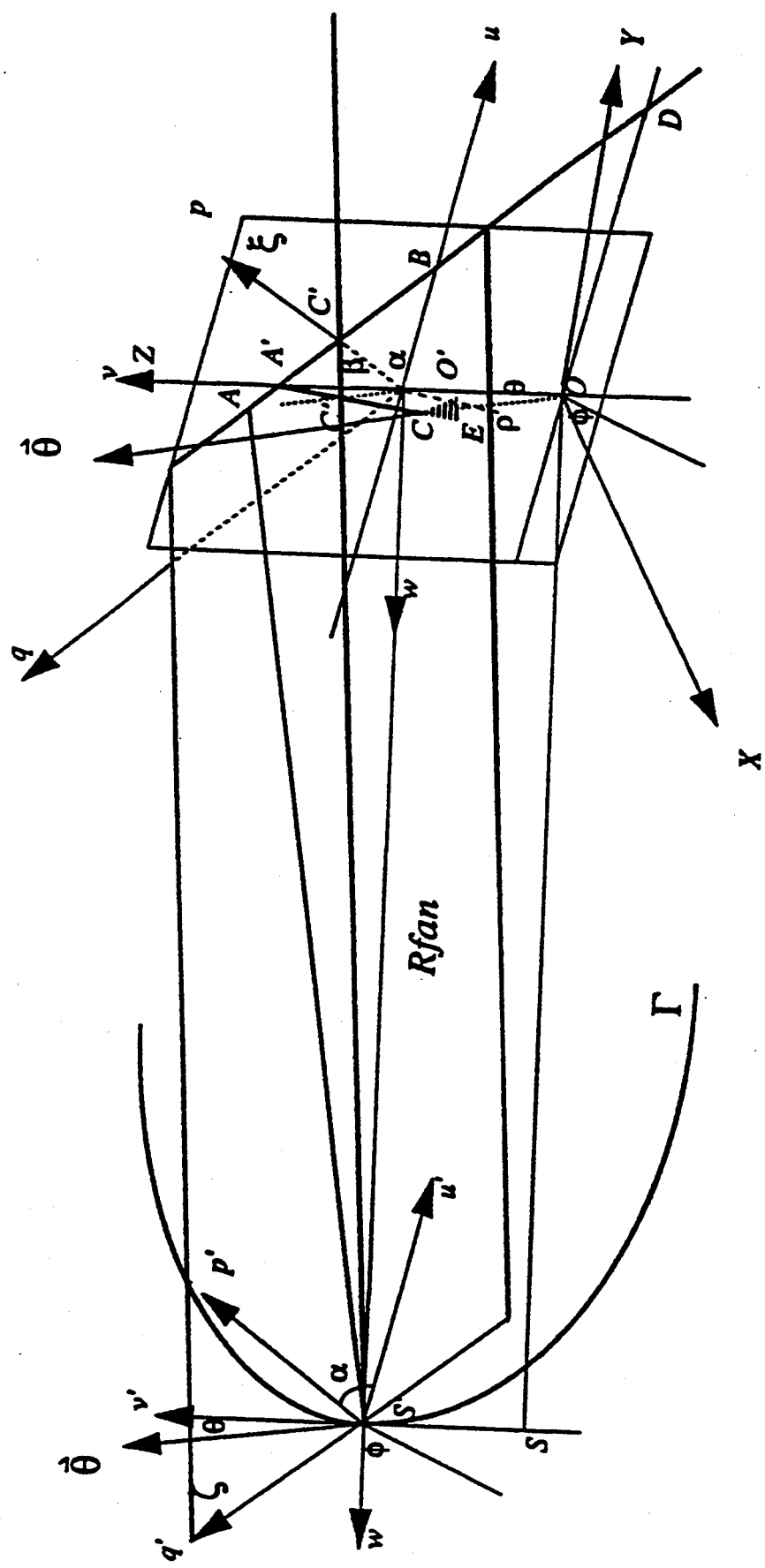
FIG. 3 illustrates a cone beam projection.

A first partial derivative means 46u takes a partial derivative of the weighted projection data G(n,u,v) with respect to the direction of axis u. A second partial derivative means 46v takes the partial derivative of the weighted projection data G(n,u,v) with respect to the direction v. A linear combining means 48 linearly combines the partial derivatives with respect to u and v. More specifically, the linear combining means includes a cosine multiplying means 50 and a sine multiplying means 52 for multiplying the partial derivatives by the cosine and sine, respectively, of an angle $\alpha$ between the axis u and an arbitrary vector direction p. An adding means 54 adds the products of the partial derivatives of the weighted projection data memory and the sine and cosine values to form a partial derivative of the projection data along the p direction, $\partial G(n,u,v)/\partial p$. See Equation (17) below. With reference to FIG. 3, this rotates the partial derivative within the plane (u,v) by $\alpha$ degrees to fall along an arbitrary vector direction p. The partial derivatives of the projection data along the vector direction p are stored in a partial derivative along the vector direction p memory means 56. Thus, the means 46–56 function as a means 58 for taking a partial derivative with respect to the vector direction p.

For simplicity, the variables of the partial derivative with respect to p have been redefined $\partial G(n,\alpha,p)/\partial p$. As explained above, u and v are related to the unit vector direction p by sine and cosine relationships of the angle $\alpha$ (see FIG. 3). However, in the (n,$\alpha$,p) coordinate system, the summation along the q vector direction is more straightforward. A coordinate transform means 60 transforms or rotates the (n,u,v) coordinate system of the partial derivative to a coordinate system (n,$\alpha$,p).

An integrating means 62 integrates or projects the data along a vector direction q which lies in the (u,v) plane perpendicular to the vector direction p. The integration is preferably performed by summing row by row or line by line to obtain a one-dimensional array along each vector direction q. See Equations (10) and (11) below. The plurality of one-dimensional arrays generated at each angle $\alpha$ are stored in a projection data memory means 64.

Figure 4:
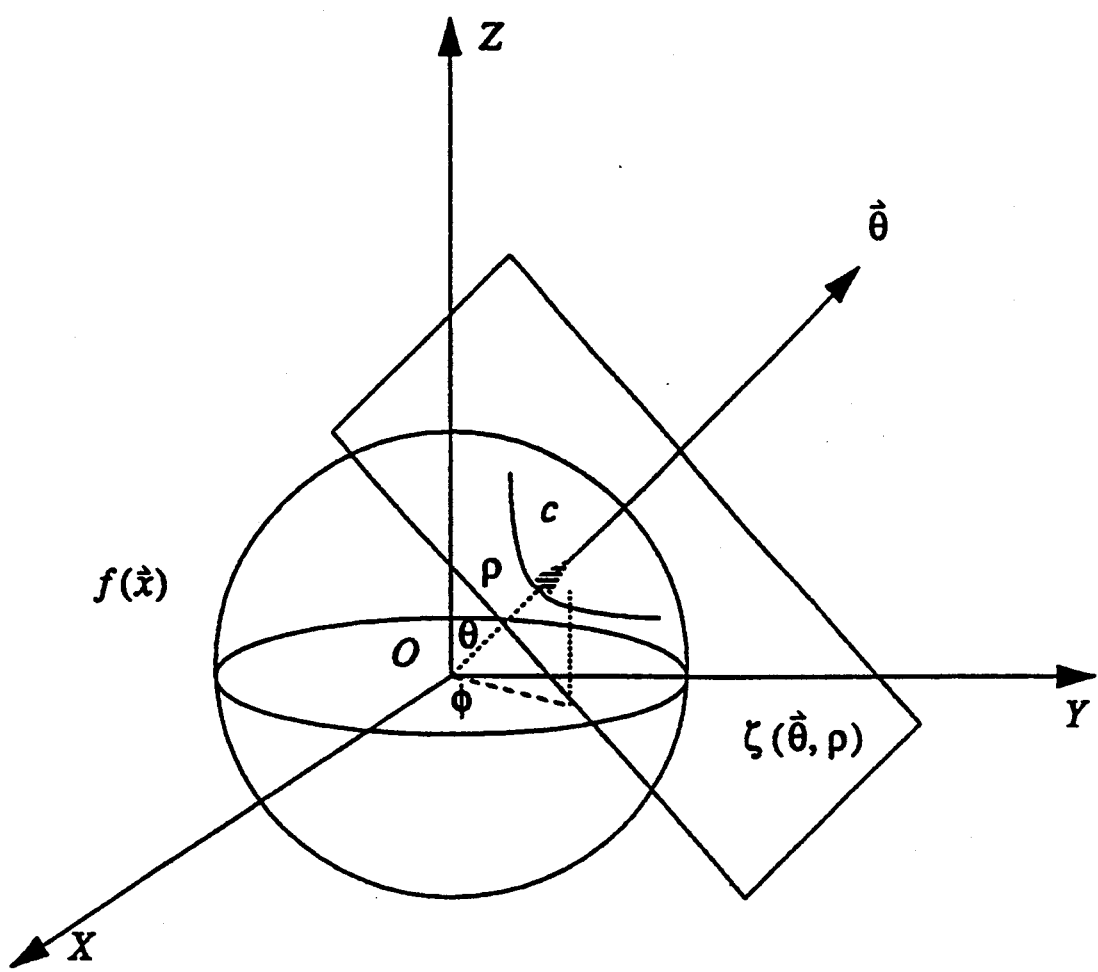
FIG. 4 is illustrative of the Radon transform.

With reference to FIG. 4, the relationship between the integrals or projection data and the first derivative of the Radon transform $R'(\vec{\theta},\rho)$ is given by Equation (12) below, where $\beta$ is the angle between lines S'C' and O'C'. A rebinning means 70 rebins or sorts the two-dimensional data arrays from the projection memory means 64 into the first derivative $R'(\vec{\theta},\rho)$ of the Radon transform for storage in a first Radon transform derivative memory means 72.

A differentiating means 74 takes the second derivative in the Radon domain to generate second derivative Radon domain data $R''(\vec{\theta},\rho)$ which is stored in a second Radon domain derivative memory means 76. A backprojecting means 80 backprojects the second Radon domain data arrays $R''(\vec{\theta},\rho)$ into a three-dimensional image representation f(x,y,z) which is stored in a three-dimensional image memory means 82. Data from the three-dimensional image memory means is selectively withdrawn for display on a video monitor 84. As is conventional in the art, planes of data may be selected and displayed. Alternately, surface renderings, projections, and other manipulations of the data may be made prior to display, as are known in the art. Data from the image memory means 82 may also be stored to disk or other archive memory means.

Looking to the theory behind the reconstruction and with reference again to FIG. 2, the cone beam projections are defined as line integrals:

$$g(S', \vec{\alpha}) = \int_{-\infty}^{\infty} f(S' + t\vec{\alpha}) dt, \tag{1}$$

where S' is the focal point on the orbit $\Gamma$ and $\vec{\alpha}$ is the unit vector of the integral line.

Using the cross point A of the integral line and the detector plane as a parameter, the cone beam projections can be written as:

$$g(S', A) = \int_{-\infty}^{\infty} f(S' + t\vec{\alpha}) dt. \tag{2}$$

Figure 2:
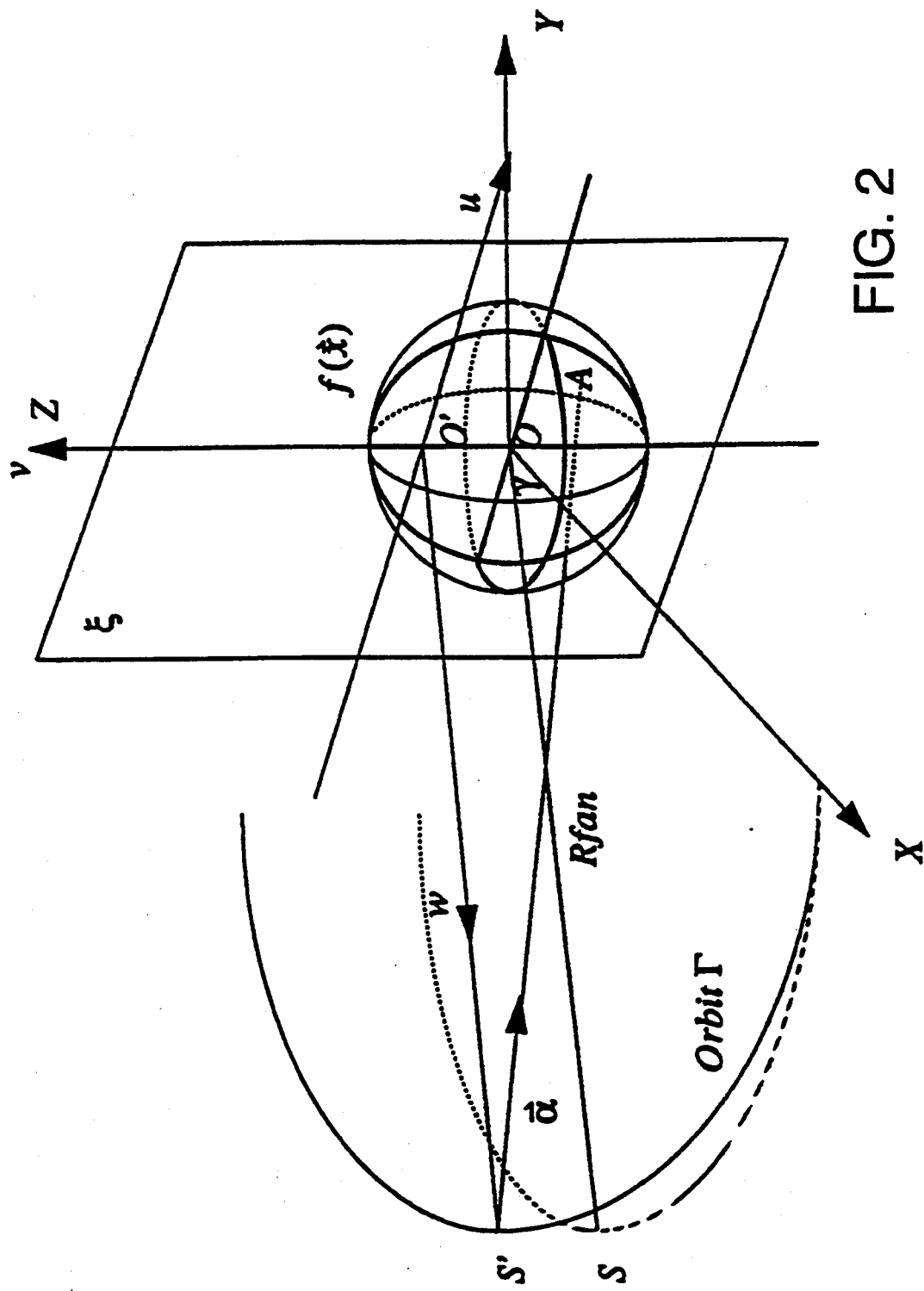
FIG. 2 illustrates the geometry of a helical scan.

In FIG. 2, $\xi$ is the detector plane, O'-uvw is the detector coordinate system, O-XYZ is the coordinate system for the object f(x,y,z), Rfan is the focal length, and $\Gamma$ is the orbit of the focal point.

With reference to FIG. 4, a 3D Radon transform $R(\vec{\theta},\rho)$ of the object f(x,y,z) for a definite $\vec{\theta}$, $\phi$, and $\rho$ is defined by the plane integral:

$$R(\vec{\theta},\rho) = \int \int_{-\infty}^{\infty} \int f(\vec{x})\delta(\vec{x}\cdot\vec{\theta} - \rho)d\vec{x}, \tag{3}$$

where $$\vec{\theta} = (\sin\theta\cos\Phi, \sin\theta\sin\Phi, \cos\theta) \tag{4}$$

is the unit vector of the normal direction of integral plane $\zeta(\vec{\theta},\rho)$.

The first derivative of the Radon transform with respect to $\rho$ is given by:

$$R'(\vec{\theta},\rho) = \frac{\partial}{\partial\rho} R(\vec{\theta},\rho). \tag{5}$$

From all the Radon transforms of an object, one can reconstruct the object exactly by using the inverse Radon transform. The inverse Radon transform can be expressed as:

$$f(\vec{x}) = -\frac{1}{4\pi^2} \int \int_{2\pi} \frac{\partial^2}{\partial\rho^2} R(\vec{\theta},\rho)\Big|_{\rho=\vec{x}\cdot\vec{\theta}} d\omega, \tag{6}$$

where:

$$d\omega = \sin\theta d\theta d\Phi. \tag{7}$$

The first derivative of the Radon transform can also be used to express the Radon inversion formula:

$$f(\vec{x}) = -\frac{1}{4\pi^2} \int \int_{2\pi} \frac{\partial}{\partial\rho} R'(\vec{\theta},\rho)\Big|_{\rho=\vec{x}\cdot\vec{\theta}} d\omega. \tag{8}$$

Thus, from the first derivatives of the Radon transforms, one can recover the object exactly. Grangeat's formula relates the cone beam projections and the first derivative of the Radon transform.

With reference to FIG. 3, consider a source position S' on the orbit $\Gamma$ and a given unit vector $\vec{\theta}$ in $2\pi$. First, the weighted cone beam projection G(S',A) is defined as:

$$G(S', A) = \frac{|\vec{SO}|}{|\vec{SA}|} g(S', A). \tag{9}$$

The integration plane $\zeta(\vec{\theta},\rho)$ is defined as the unique plane perpendicular to the vector $\vec{\theta}$ and crossing S'. The point C, the orthogonal projection of the origin O on this plane, is called its characteristic point. OC=$\rho$. Line AA'C'BD is the cross line of integration plane $\zeta$ and detector plane $\xi$. Notice that C' is the orthogonal projection of the origin O' on the line AA'C'BD. Line O'C' is perpendicular to the line AA'C'BD. Connecting S' and C' gives S'C'. From O', draw O'C" perpendicular to S'C'. It is very easy to prove that O'C" is parallel to the OC and both of them are perpendicular to the plane $\zeta$. One can also show that the points C, C", and A' are in the same line. There are now three coordinate systems: O-XYZ is the coordinate system for the object f(x,y,z) and its Radon transform, O'-uvw is the coordinate system for the focal point and the detector plane, and O'-pqw is the rotation of O'-uvw along axis w by an angle $\alpha$ to set axis p perpendicular to the line AA'C'BD, hence the integration plane.

The SG(S',$\vec{\theta}$) is defined as the integration of the weighted cone beam projection G(S',A) over the integration line AA'C'BD:

$$SG(S',\vec{\theta}) = \int_{(A\in \text{Line} AA'C'BD)} G(S', A) dA. \tag{10}$$

The coordinates system O'-pqw can also be used to express the integral above as:

$$SG(S', \vec{\theta}) = \int_{-\infty}^{\infty} G(S', \vec{OC} + q\vec{q}) dq, \tag{11}$$

where q is the unit vector of the axis q.

Grangeat's formula gives the fundamental relation between the cone beam projection and the first derivative of the Radon transform $R'(\theta,\rho)$:

$$\frac{1}{(\sin\beta)^2} \frac{\partial}{\partial p} SG(S',\vec{\theta}) = R'(\vec{\theta}, \rho), \quad (12)$$

where $\beta$ is the angle between line S'C' and O'C', the left hand side of the Equation is in the cone beam projection domain, and the right hand side is in the Radon domain.

It is known that if the focal point follows a planar orbit, then the data obtained does not satisfy Tuy's sufficiency condition for exact three-dimensional reconstruction. Tuy's sufficiency condition says: If any plane that intersects the object f(x,y,z) intersects the orbit of the focal point and the detector plane at the same time at least once there is enough cone beam projection data to recover f(x,y,z). A helical orbit of measurement fulfills Tuy's condition.

For example, a helical orbit with a pitch of 32 is selected with 64 views of projection data generated for each pitch. Thus, two pitches provide 128 views of projections which are uniformly distributed on the orbit. In the present example, the O-XYZ is the coordinate system of the object f(x,y,z) which now is the Defrise phantom. In the O-XYZ system the Equation of the helical orbit $\Gamma$ can be written as:

$$\begin{bmatrix} x \\ y \\ z \end{bmatrix} = \begin{bmatrix} Rfan \cdot \cos\gamma \\ Rfan \cdot \sin\gamma \\ \gamma \frac{16}{\pi} - 32 \end{bmatrix}, \quad (13)$$

where $\gamma$ is the parameter of the Equation. It is the angle between the orthogonal projection of the focal point to the O-XY plane and the x axes, as shown in FIG. 2.

In the coordinate system O-XYZ, the Equation of the integral plane $\zeta(\vec{\theta},\rho)$ is expressed as:

$$\vec{x} \cdot \vec{\theta} = \rho. \quad (14)$$

By using Equation (4), Equation (14) can be written as:

$$x \sin\theta \cos\phi + y \sin\theta \sin\phi + z \cos\theta - \rho = 0. \quad (15)$$

The focal point positions $\gamma$ (views) are obtained by solving Equations (13) and (15) for given point $(\vec{\theta},\rho)$.

With reference to FIG. 1, the helical cone beam projection data g(S',A) is stored in the three-dimensional array g(n,u,v) in the data memory 40, where n from 1 to 128 is the view of projection which means the location of point S', u, and v are horizontal and vertical components of point A in the detector plane. The detector plane in the present example is a 64×64 two-dimensional array.

The projection data g(n,u,v) is scaled by means 42 to G(n,u,v) as per Equation (9).

In order to use Grangeat's formula (12), the $\partial G(n,u,v)/\partial p$ of G(n,u,v) is obtained. It is known that:

$$\frac{\partial}{\partial p} SG(S',\vec{\theta}) = \frac{\partial}{\partial p} \int_{-\infty}^{\infty} G(S', \overrightarrow{OC} + \vec{qq})dq = \quad (16)$$

$$\int_{-\infty}^{\infty} \frac{\partial}{\partial p} G(S', OC + qq)qd,$$

where $G(S',OC'+\vec{qq})$ can be expressed as G(n,u,v).

First, the partial derivative with respect to the p is calculated by means 58 and then the integral along the q direction is calculated by means 62.

For the given tilt, angle $\alpha$ of the axis $\rho$, the partial derivative in the direction p is given by:

$$\frac{\partial}{\partial p} G(n,u,v) = \cos\alpha \frac{\partial}{\partial u} g(n,u,v) + \sin\alpha \frac{\partial}{\partial v} G(n,u,v), \quad (17)$$

which is calculated by means 46u, 46v, and 48. The line integral along AA'C'BD $$\int_{-\infty}^{\infty} \frac{\partial}{\partial p} G(n,u,v)dq$$

can be evaluated by using the algorithm described by P. M. Joseph in "An Improved Algorithm For Reprojecting Rays Through Pixel Images", IEEE Trans on Med Imaging MI-1, (3) 192–196. After the calculation above, the three-dimensional array $\Sigma \partial G(n,\alpha,p)/\partial p$ is calculated 62 and stored in memory means 64, where n is the index of the views, $\alpha\epsilon[0°, 180°]$ is the tilt angle of the axis p, p is the coordinate in the p axis of the detector coordinate system O-pqw, $\Sigma \partial G(n,\alpha,p)/\partial p$ is the first derivative along p axis of the projection at (n,$\alpha$,p).

The rebinning means 70 converts the three-dimensional array $\Sigma \partial G(n,\alpha,p)/\partial p$ to the three-dimensional array $R'(\vec{\theta},\rho)$ in the Radon domain which is the first derivative of Radon transform of f(x,y,z) at $(\vec{\theta},\rho)$ in the coordinate O-XYZ.

With reference to FIG. 3, from given point $(\vec{\theta},\rho)$ and Rfan one can solve Equations (13) and (15) for S', or at least one point of S'. This can be converted to n (the views of projection). Line OO' is the Z component of the point S'. Now one uses $(\vec{\theta},\rho)$ and OO' to express p and $\alpha$. From FIG. 3, it can be seen that:

$$O'C'' = \rho - OO' \cos\theta \quad (18),$$

and because of $O'C'' \perp S'C''$:

$$p = O'C = \frac{O'C'}{\sin\beta} = \frac{Rfan}{(Rfan^2 - O'C''^2)^{1/2}}, \quad (19)$$

where O'C'' is given by Equation (18). Similarly, the expression of angle $\alpha$ is:

$$\alpha = \sin^{-1}\left(\frac{p}{\frac{\rho}{\sin\theta} - OO'}\right). \quad (20)$$

Equations (19) and (20) are the rebinning equations which are performed by the rebinning means 70. The rebinning means 70 further solves Equations (13), (15) and uses Grangeat's formula to get the first derivative of Radon transform $R'(\vec{\theta},\rho)$ that is stored in memory 72.

The first rebinning technique finds (n,$\alpha$,p) for given $(\vec{\theta},\rho)$, i.e. maps to the cone beam domain from the Radon domain. An alternative rebinning technique finds $(\vec{\theta},\rho)$ for given (n,$\alpha$,p), i.e. maps to the Radon domain from the cone beam domain. From FIG. 3, it is apparent that:

$$O'C \cdot Rfan = O'C' \cdot \sqrt{(Rfan)^2 + (O'C)^2}. \quad (21)$$

That is:

$$O'C' = \frac{O'C \cdot R_{fan}}{\sqrt{(R_{fan})^2 + (O'C)^2}}. \quad (22)$$

From FIG. 3, it is also apparent that:

$$\frac{\rho}{O'C'} = \frac{A'O' + OO'}{A'O'} = 1 + \frac{OO'}{A'O'}. \quad (23)$$

Solving for $\rho$ gives:

$$\rho = O'C'\left(1 + \frac{OO'}{A'O'}\right) = O'C'\left(1 + \frac{OO'\sin\alpha}{O'C}\right). \quad (24)$$

By using Equation (22), Equation (24) can be written as:

$$\rho = \frac{R_{fan}}{\sqrt{(R_{fan})^2 + (O'C)^2}}(O'C + OO'\sin\alpha). \quad (25)$$

Because O'C' is just p and OO' is easy to get by a given n, one can get $\rho$ by solving Equation (25).
First, the angle $\theta$ is calculated:

$$\cos\theta = \frac{O'C'}{O'A'} = \frac{R_{fan} \cdot \sin\alpha}{\sqrt{R_{fan}^2 + O'C^2}}. \quad (26)$$

Solving for $\theta$:

$$\theta = \text{acos}\left(\frac{R_{fan} \cdot \sin\alpha}{\sqrt{R_{fan}^2 + O'C^2}}\right). \quad (27)$$

The next step is to calculate the angle $\phi$. Because the point S' is on the plane $\zeta$ of FIG. 3:

$$\overrightarrow{OS'} \cdot \vec{\theta} = \rho \quad (28).$$

Combining this Equation with Equation (4) and Equation (13):

$$R_{fan} \cdot \sin\theta \cdot \cos(\gamma - \phi) = \rho + \left(32 - \gamma \frac{16}{\pi}\right) \cdot \cos\theta. \quad (29)$$

Giving the expression for $\phi$:

$$\phi = \gamma - \text{acos}\left(\frac{\rho + \left(32 - \gamma \frac{16}{\pi}\right) \cdot \cos\theta}{R_{fan} \cdot \sin\theta}\right), \quad (30)$$

where $\gamma$ is obtained from a given n. Equations (25), (26), and (30) form the second rebinning equation set, which enables one to obtain the first derivative of Radon transform $R'(\vec{\theta},\rho)$ by using Grangeat's formula.

From $R'(\vec{\theta},\rho)$, the second derivative means 76 takes the second derivative and the backprojection means 78 backprojects the second derivative to get the object f(x,y,z). In summary, the reconstruction scheme is:

$$g(n,u,v) \to G(n,u,v) \to \frac{\partial}{\partial p} G(n,u,v) \to \frac{\partial}{\partial p} G(n,u,v) \quad (31)$$

$$\to \Sigma \frac{\partial G(n,\alpha,p)}{\partial p} \to R'(\vec{\theta},\rho) \to R''(\vec{\theta},\rho) \to f(\vec{x}).$$

Because the helical orbit produces a complete set of data, an artifact-free image can be reconstructed.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An apparatus for generating an image representation of an interior portion of a subject, the apparatus comprising:
   a radiation detection means for receiving radiation travelling along a cone of rays which converge at a focal point and for generating electrical data indicative thereof;
   a means for moving the radiation detecting means such that the focal point moves in a helical orbit and the radiation detection means generates helical orbit data;
   a partial derivative means for generating a partial derivative of the helical orbit data with respect to an arbitrary direction in a plane of the detector means;
   an integrating means for projecting the derivative along a direction perpendicular to the arbitrary direction in the detector plane;
   a rebinning means for rebinning the projections into first derivative Radon domain data;
   a second derivative means for generating a second derivative of the Radon domain data;
   a backprojecting means for reconstructing the second derivative Radon domain data into a three-dimensional image representation;
   an image memory means for storing the three-dimensional image representation.

2. The apparatus as set forth in claim 1 wherein the rebinning means includes a means for mapping from preselected points in a cone beam domain to corresponding points in the first derivative Radon domain.

3. The apparatus as set forth in claim 1 wherein the rebinning means includes a means for mapping from preselected points in the first derivative Radon domain to corresponding points in a cone beam domain.

4. The apparatus as set forth in claim 1 including a monitor means for converting a portion of the image representation into a human readable display.

5. The apparatus as set forth in claim 1 further including a scaling means for scaling the helical data, the scaling means being disposed between radiation detection means and the partial derivative means.

6. The apparatus as set forth in claim 1 wherein the partial derivative means include:
   a first partial derivative means for taking a partial derivative along a horizontal direction;
   a second partial derivative means for taking a partial derivative along a vertical direction; and
   a linear combining means for linearly combining the partial derivatives along the horizontal and vertical directions to produce the partial derivative along the arbitrary direction.

7. The apparatus as set forth in claim 6 wherein the linear combining means includes a means for multiplying the partial derivatives along the vertical and horizontal directions with sine and cosine values of an angle between one of the horizontal and vertical directions and the arbitrary direction in the detector plane.

8. The apparatus as set forth in claim 7 wherein for each angle, the integrating means sums row by row to produce a one-dimensional array.

9. A method for generating an image representation of an interior portion of a subject, the method comprising:
   generating cone beam electrical data from detected radiation travelling along a cone of rays which converge at a focal point, the radiation being detected by a radiation detection means along a detection plane;
   moving the radiation detecting means such that the focal point moves in a helical orbit;
   taking a partial derivative of the electrical data with respect to an arbitrary direction along the detection plane;
   projecting the partial derivative along a direction perpendicular to the arbitrary direction along the detection plane;
   rebinning the projections into first derivative Radon domain data;
   taking a second derivative of the Radon domain data;
   backprojecting the second derivative Radon domain data into a three-dimensional image representation;
   converting at least a portion of the image representation into a human readable display.

10. The method as set forth in claim 9 further including storing the three-dimensional image representation.

11. The method as set forth in claim 9 further including scaling the electrical data prior to taking the partial derivative along the arbitrary direction in the detection plane.

12. The method as set forth in claim 9 wherein the rebinning includes mapping from preselected points of the projected partial derivative electrical data along the detection plane to corresponding points in the first derivative Radon domain.

13. The method as set forth in claim 9 wherein the rebinning includes mapping from preselected points in the first derivative Radon domain to corresponding points on the detection plane.

14. The method as set forth in claim 9 wherein taking the partial derivative includes:
   taking a partial derivative along a horizontal direction;
   taking a partial derivative along a vertical direction;
   linearly combining the partial derivatives along the horizontal and vertical directions to produce the partial derivative along the arbitrary direction.

15. The method as set forth in claim 14 wherein the linear combining includes multiplying the partial derivatives along the vertical and horizontal directions with sine and cosine values of an angle between one of the horizontal and vertical directions and the arbitrary direction in the detection plane.

16. The method as set forth in claim 15 wherein for each angle, the projecting step includes summing row by row to produce one-dimensional arrays which are rebinned.

17. A method for generating an image representation of an interior portion of a subject, the method comprising:
   generating cone beam electrical data from detected radiation travelling along a cone of rays which converge at a focal point, the radiation being detected along a detection plane such that the focal point moves along a helical orbit;
   taking partial derivatives of the electrical data with respect to an arbitrary direction along the detection plane;
   projecting the partial derivative along a direction perpendicular to the arbitrary direction along the detection plane;
   determining points in a Radon domain which correspond to preselected points in the detection plane;
   mapping the projected partial derivatives into first derivative Radion domain data;
   generating second derivative Radon domain data from the first derivative Radon domain data;
   backprojecting the second derivative Radon domain data into a three-dimensional image representation;
   converting at least a portion of the image representation into a human readable display.

* * * * *